United States Patent [19]
Jenkins, Jr.

[11] Patent Number: 5,571,139
[45] Date of Patent: Nov. 5, 1996

[54] BIDIRECTIONAL SUTURE ANCHOR

[76] Inventor: Joseph R. Jenkins, Jr., 12203 Becontree Dr., Baton Rouge, La. 70810

[21] Appl. No.: 445,337

[22] Filed: May 19, 1995

[51] Int. Cl.⁶ .................................................. A61B 17/00
[52] U.S. Cl. ........................ 606/232; 606/65; 606/73; 623/13
[58] Field of Search ........................ 606/53, 60, 65, 606/67, 72, 73, 76, 77, 232, 75; 623/13

[56] References Cited

U.S. PATENT DOCUMENTS

| | | | |
|---|---|---|---|
| 4,711,232 | 12/1987 | Fischer et al. | 606/67 |
| 5,156,616 | 10/1992 | Meadows et al. | 606/232 |
| 5,354,299 | 10/1994 | Coleman | 606/73 |
| 5,364,400 | 11/1994 | Rego, Jr. et al. | 606/73 |
| 5,456,685 | 10/1995 | Huebner | 606/73 |
| 5,486,197 | 1/1996 | Le et al. | 606/232 |

OTHER PUBLICATIONS

*A New Bone Anchor for Re–Attachment of Soft Tissue and Management of Fractures and Dislocations, Surgery Technology Int'l III*, Nov. 1994, pp. 593–602; William S. Ogden.
Acumed, Inc., Beaverton, Oregon; promotional brochure for Acutrak headless compression screw system; Jan. 17, 1994.

*Primary Examiner*—Michael Powell Buiz
*Assistant Examiner*—Jeffrey A. Schmidt
*Attorney, Agent, or Firm*—Warner J. Delaune

[57] ABSTRACT

A cannulated bone screw for anchoring bidirectional suture threads to bone is provided, comprising a biocompatible body having a proximal end and a distal end, the body including exterior screw threads, preferably self-tapping, for inserting and retaining the body into the bone; a passageway extending through the body, the passageway including a central portion, a proximal portion, and preferably a distal portion, the central portion being sized to receive a suture thread therethrough, the proximal and distal portions each being sized to receive a suture thread knot, the central portion being sized smaller than the proximal and distal portions, the central portion being sufficiently small as to prevent a suture thread knot from being drawn therethrough; and a drive socket, formed into the proximal end of the body, the drive socket being sized to prevent a drive tool from contacting a suture thread knot within the proximal portion of the passageway. The body of the bone screw may be either cylindrical in shape, or it may be tapered with variably pitched screw threads. The bone screw is constructed of a biocompatible material, such as a metal, a non-absorbable polymer, or a bioabsorbable material, where the biocompatible material is coated with a bioabsorbable coating having a low coefficient of friction. The bioabsorbable coating may include one or more compounds, such as a pharmaceutical or selected bone growth factors. A method for using the bidirectional bone screw is also provided.

8 Claims, 6 Drawing Sheets

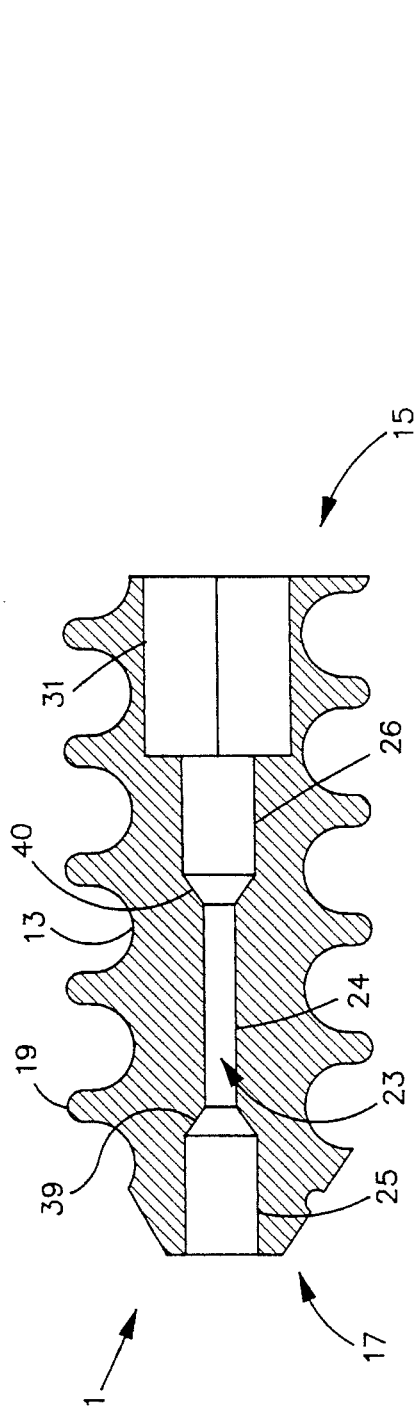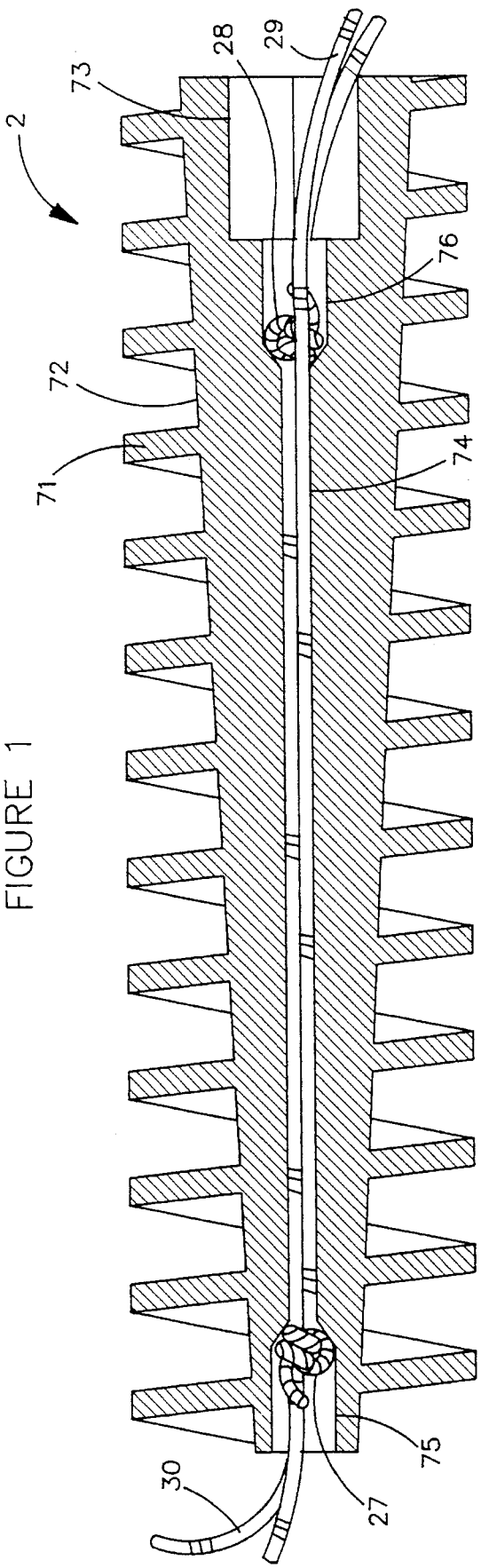

BIDIRECTIONAL SUTURE ANCHOR

BACKGROUND OF THE INVENTION

I. Field of the Invention

The present invention relates generally to devices and methods for attaching soft tissue to bone, and more particularly to devices for anchoring sutures into the bone so that soft tissue can be attached thereto.

II. Description of Prior Art

In the field of orthopedic surgery, there are occasions when a ligament must be reattached to bone. For example, the ligaments surrounding the shoulder, elbow or knee may become detached from the bone due to a traumatic injury. Repair of these types of damages and restoration of the function of the ligament depends heavily on the extent to which the ligament is allowed to grow back into the bone from which it has become separated. In view of the difference in density between the tissues involved, conventional suturing of the ligament to the bone must often be augmented by the use of anchoring devices which are forcibly inserted into the bone. These anchoring devices, which are capable of holding a desired length of suture thread, are generally constructed of a biocompatible metal or possibly an absorbable material. Depending upon the type of anchor employed, the suture is either attached to the anchor prior to insertion, or it may be attached after the anchor is implanted into the bone. In either case, once the suture and anchor are in place, the suture extending from the anchor is then used to tie the ligament against the bone in a manner which allows the ligament to grow into the bone mass.

One such device and method for suture attachment is disclosed in U.S. Pat. No. 5,156,616 issued to Meadows and Ogden (hereinafter "Ogden"), the disclosure of which is incorporated herein by reference. The device comprises a cannulated bone screw constructed of a biocompatible metal, wherein the body includes exterior screw threads for inserting and retaining the screw into bone. A passageway extends completely through the body of the screw, where the passageway is divided into a central portion and a distal portion. The central portion and distal portion of the passageway are both large enough to accommodate the size of suture threads. However, the distal portion is larger than the central portion in order to accept a suture thread knot. Thus, the relative sizes of the central portion and the distal portion are such that the suture thread knot can be held within the distal portion, but prevented from passing through the central portion. Opposite from the distal portion, the screw also includes means for cooperating with an external drive tool to drive the screw into the bone, such as a hexagon- or square-shaped socket. The driving tool is also cannulated or slotted, which protects the suture threads extending from the proximal portion from being damaged during insertion. As an alternative, a longitudinal groove may be formed into the side of the socket adjacent to the path of the tool to achieve the same purpose.

In operation of the Ogden anchor, suture thread is passed through the passageway so that a part of the suture extends beyond the distal portion of the screw. The excess suture is tied into a knot and then pulled through the passageway until the knot becomes seated within the distal portion and abuts the central portion of the passageway. The screw is then placed into the bone after the formation of a suitable pilot hole.

While the Ogden anchor does appear to provide favorable results, it fails to provide "bidirectional" anchoring. As used herein, the term "bidirectional" means the capability of a cannulated screw to safely accommodate suture threads extending from either (or both) the distal or (and) proximal portion of the screw. Specifically, the anchored sutures in Ogden may only extend from the proximal portion of the screw, because the suture knot must be contained within the distal portion of the passageway. In the existing design for the Ogden anchor, as seen in FIGS. 2, 5, and 6 of that reference, there are no structural features which can safely accommodate a proximal knot and distally extending suture threads. Although there is a cavity present at the proximal end of the Ogden anchor, it is intended exclusively for receiving an external driving tool to insert the screw into the bone. Thus, the drive socket is not designed to accept a suture thread knot.

For example, a suture knot placed into the Ogden drive socket (prior to the modifications disclosed herein) would create at least two detrimental effects. First, the presence of any obstruction in the drive socket (such as a knot) would hinder the insertion of the anchor into the bone, because there would be less contact between the socket and the driving tool. This condition can result in misalignment of the anchor, and it can cause damage to surrounding tissue if the tool should slip from the socket during insertion. Second, the pressure of the metal driving tool is often quite high as the self-tapping screw threads of the anchor are urged into the cancellous bone. If a suture knot were pinched between the drive socket and the tool, the suture threads may be damaged or completely severed, thus jeopardizing the critical tensile strength of the threads.

The same limitations seen in the Ogden anchor can also be found in certain bone fixation screws. For example, in the bone fixation screw manufactured by Acumed, Inc., and marketed under the trade name "Acutrak", a headless compression screw with variable pitch threads is used to join fractured bone fragments. This device is also cannulated to allow its insertion over a guide pin. although it lacks the ability to receive suture threads as explained by Ogden. While the Acutrak device is well-suited to rejoining cancellous bone, its utility would be greatly enhanced if an Ogden-type suture anchoring feature were implemented. Moreover, modification of the Acutrak device to include "bidirectional" suture anchoring would undoubtedly increase its advantages in bone fixation applications.

Therefore, the present invention builds upon the utility of the Ogden anchor and the Acutrak bone fixation screw by the combined use of a distal recess at the insertion end of either device, as well as a proximal recess formed below the drive socket. The proximal recess in both cases would be similar in size and shape to the distal recess described in the Ogden reference, and it would permit the placement of suture thread extending from the distal end of either screw. Moreover, as the central passageway may be sized to accommodate multiple threads, the invention is quite advantageous in situations which may require sutures extending from both ends of the anchor or fixation screw, as the case may be. This simple, yet critically important, modification to the foregoing prior art devices safely allows their use in a wider variety of surgical procedures, as will be explained in greater detail below.

SUMMARY OF THE INVENTION

It is therefore an object of this invention to provide a bidirectional suture anchor which allows sutures to extend from either or both ends of the anchor.

Another object of this invention is to provide a bidirectional suture anchor which can be manufactured quickly and inexpensively by the modification of an existing anchor.

It is also an object of this invention to provide a bidirectional suture anchor which can be used in a wider variety of surgical procedures than existing anchors.

It is a further object of this invention to provide a bidirectional suture anchor which affords stronger and more reliable anchoring for sutures.

These and other objects and advantages of the present invention will no doubt become apparent to those skilled in the art after having read the following description of the preferred embodiment which are contained in and illustrated by the various drawing figures.

Therefore, in a preferred embodiment, a cannulated bone screw for anchoring a suture thread to bone is provided, comprising a biocompatible body having a proximal end and a distal end, said body including exterior screw threads, preferably self-tapping, for inserting and retaining said body into the bone; a passageway extending through said body, said passageway including a central portion and a proximal portion, the central portion being sized to receive a suture thread therethrough, the proximal portion being sized to receive a suture thread knot, the central portion being sized smaller than the proximal portion, the central portion being sufficiently small as to prevent a suture thread knot from being drawn therethrough; and a drive socket, formed into said proximal end of said body, said drive socket being sized to prevent a drive tool from contacting a suture thread knot within said proximal portion of said passageway. Preferably, the passageway also includes a distal portion analogous in structure and function to the proximal portion, although for retaining a second suture thread extending in the opposite direction from the suture threads seated in the proximal portion.

The body of the bone screw may be either cylindrical in shape, or it may be tapered with variably pitched screw threads. The bone screw is constructed of a biocompatible material selected from the group consisting of a metal, a non-absorbable polymer, and a bioabsorbable material, wherein said biocompatible material is coated with a bioabsorbable coating having a low coefficient of friction. The bioabsorbable coating may include one or more compounds, such as a pharmaceutical or selected bone growth factors.

Also provided is a method for attaching suture thread to bone which employs the aforedescribed bone screw, comprising the steps of passing a first suture thread through the passageway of the body of said bone screw to extend from the proximal end; tying a first knot in the first suture thread extending from the proximal end of the passageway; withdrawing the first suture thread from the distal end of said bone screw until said first knot is received by the proximal portion and said first knot abuts the central portion; passing said first suture thread through a pilot hole in said bone; and inserting said bone screw into the bone. Optionally, in the embodiment of the invention which includes a distal portion, and prior to passing the first suture thread through the pilot hole, the method may further comprise the steps of passing a second suture thread through the passageway of the body of said bone screw to extend from the distal end; tying a second knot in the second suture thread extending from the distal end of the passageway; and withdrawing the second suture thread from the proximal end of said bone screw until said second knot is received by the distal portion and said second knot abuts the central portion.

BRIEF DESCRIPTION OF THE DRAWINGS

FIG. 1 is a sectional view of a preferred embodiment of a bidirectional suture anchor.

FIG. 2 is a sectional view of an alternative embodiment of a bidirectional suture anchor which can also be used for bone fixation.

DETAILED DESCRIPTION OF THE PREFERRED EMBODIMENT

The following description of the present invention, at least insofar as it relates to the embodiment shown in FIG. 1, incorporates by reference the entire disclosure in U.S. Pat No. 5,156,616. Any additional or different features of the present invention not disclosed in that reference are described in detail below. To the extent that any conflict exists between this description and the disclosures contained within the incorporated reference, this description shall take precedence.

Figure 3A:
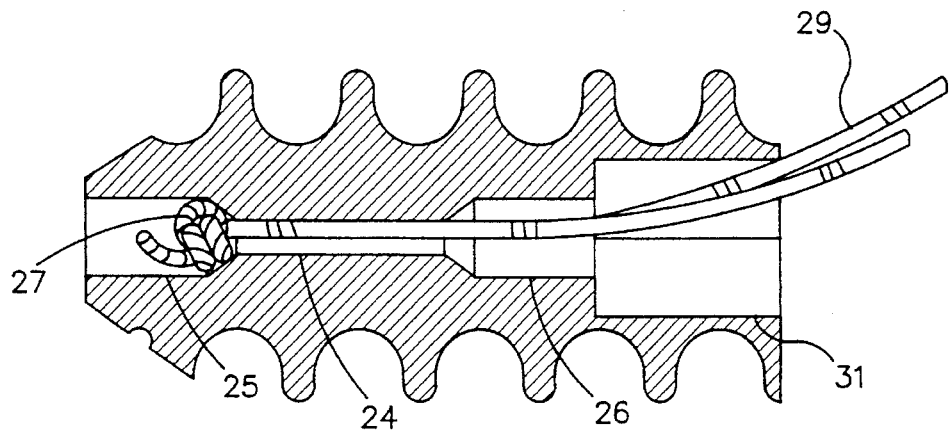
FIG. 3A is a sectional view of the embodiment of FIG. 1 depicting sutures anchored at the distal end of the anchor.
Figure 3B:
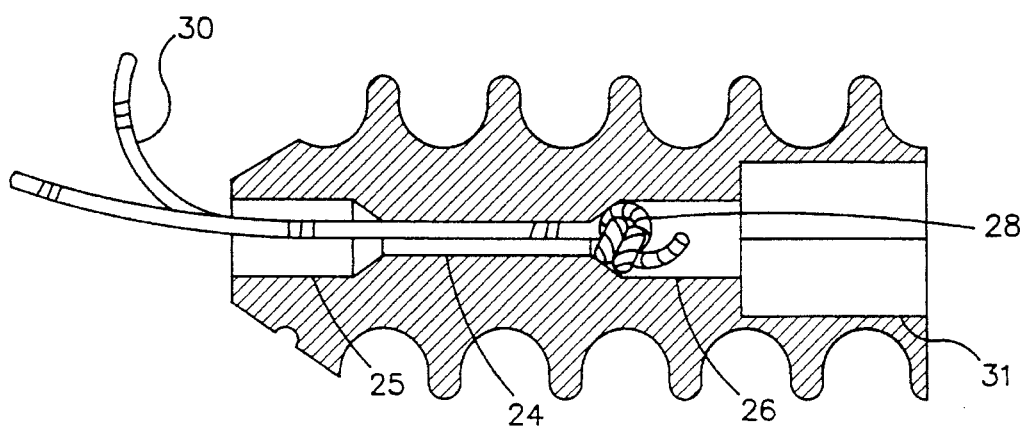
FIG. 3B is a sectional view of the embodiment of FIG. 1 depicting sutures anchored at the proximal end of the anchor.
Figure 3C:
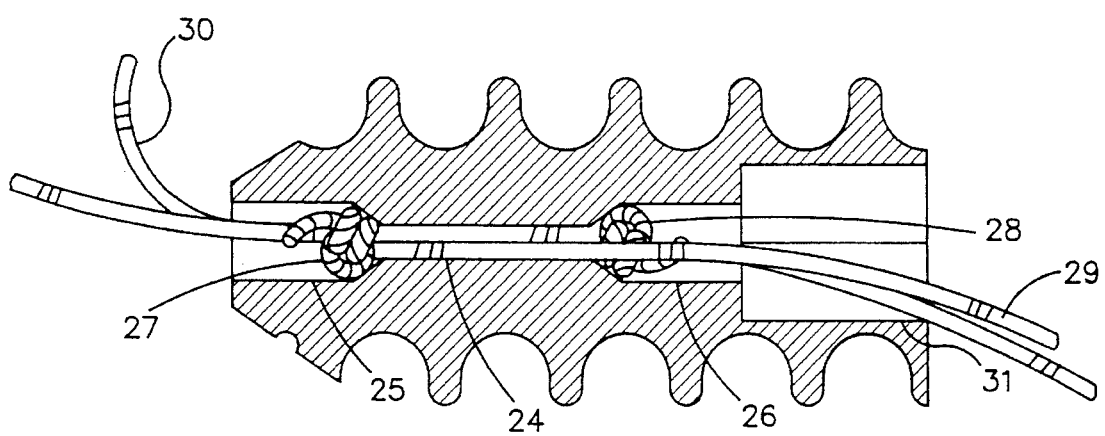
FIG. 3C is a sectional view of the embodiment of FIG. 1 depicting sutures anchored at both the distal end and proximal end of the anchor.

With reference to FIGS. 1 and 3A–3C, a preferred embodiment 1 of the present invention is shown to comprise a biocompatible body 13 having a proximal end 15 and a distal end 17. Exterior screw threads 19 are formed about the length of body 13, and include a cutting edge (not shown) which allows the threads 19 to be self-tapping. A passageway 23 is formed axially through body 13, and includes a central portion 24, a distal portion 25, and a proximal portion 26. The central portion 24 is sized to receive at least four strands of suture thread, such as first suture thread 29 or second suture thread 30, or both. It will be understood that the size of central portion 24 may be manufactured to accommodate any number of suture threads as needed for particular surgical procedures. The distal portion 25 is sized to receive a first suture thread knot 27, as shown in FIG. 3A. Likewise, proximal portion 26 is sized to receive a second suture thread knot 28, as shown in FIG. 3B. In order to prevent the passage of either suture thread knot 27,28 through central portion 24, the cross-sectional size of central portion 24 is sufficiently smaller than that of either distal portion 25 or proximal portion 26. First beveled portion 39 is formed at the base of distal portion 25, and second beveled portion 40 is similarly formed at the base of proximal portion 26, to allow suture thread knots 27,28 to become compressed as tension is applied to suture threads 29,30. FIG. 3C depicts the preferred embodiment with both first and second suture threads 29,30 in place within central portion 24, along with their respective suture thread knots 27,28 seated within distal portion 25 and proximal portion 26, respectively.

Similar to the Ogden anchor, the preferred embodiment also includes drive socket 31, which can be a square-shaped, hexagonally-shaped, or any shaped cavity which is capable of receiving a similarly shaped driving tool (not shown). Because of the presence of proximal portion 26 adjacent to drive socket 31, it is critical that drive socket 31 be sized to prevent a driving tool from contacting second suture thread knot 28 while the anchor is inserted into the bone. Avoidance of such detrimental contact is required to ensure the integrity of suture thread 30. In comparison, the Ogden reference does not permit the placement of second suture thread 30 and its accompanying knot 28 in this position, because the drive tool would necessarily apply damaging pressure against the knot 28.

Use of the preferred embodiment is similar to the use of the Ogden anchor. In fact, if the invention is applied only with first suture thread 29, the procedure for its application is identical to the prior art. However, if the invention is applied only with second suture thread 30, the procedure is essentially reversed. For example, second suture thread 30 is passed through the central portion 24 of passageway 23 with an exposed section thereof protruding from proximal end 15. Next, second suture thread knot 28 is tied in the exposed section of second suture thread 30. Second suture thread 30 is then drawn through passageway 23 from the distal end 17 until second suture thread knot 28 is firmly seated within proximal portion 26 against the smaller cross-sectional diameter of central portion 24. Therefore, it will be understood that the use of both first and second suture threads 29,30 would simply involve the foregoing procedure in combination with the procedure explained in the Ogden reference for first suture thread 29.

Figure 4A:
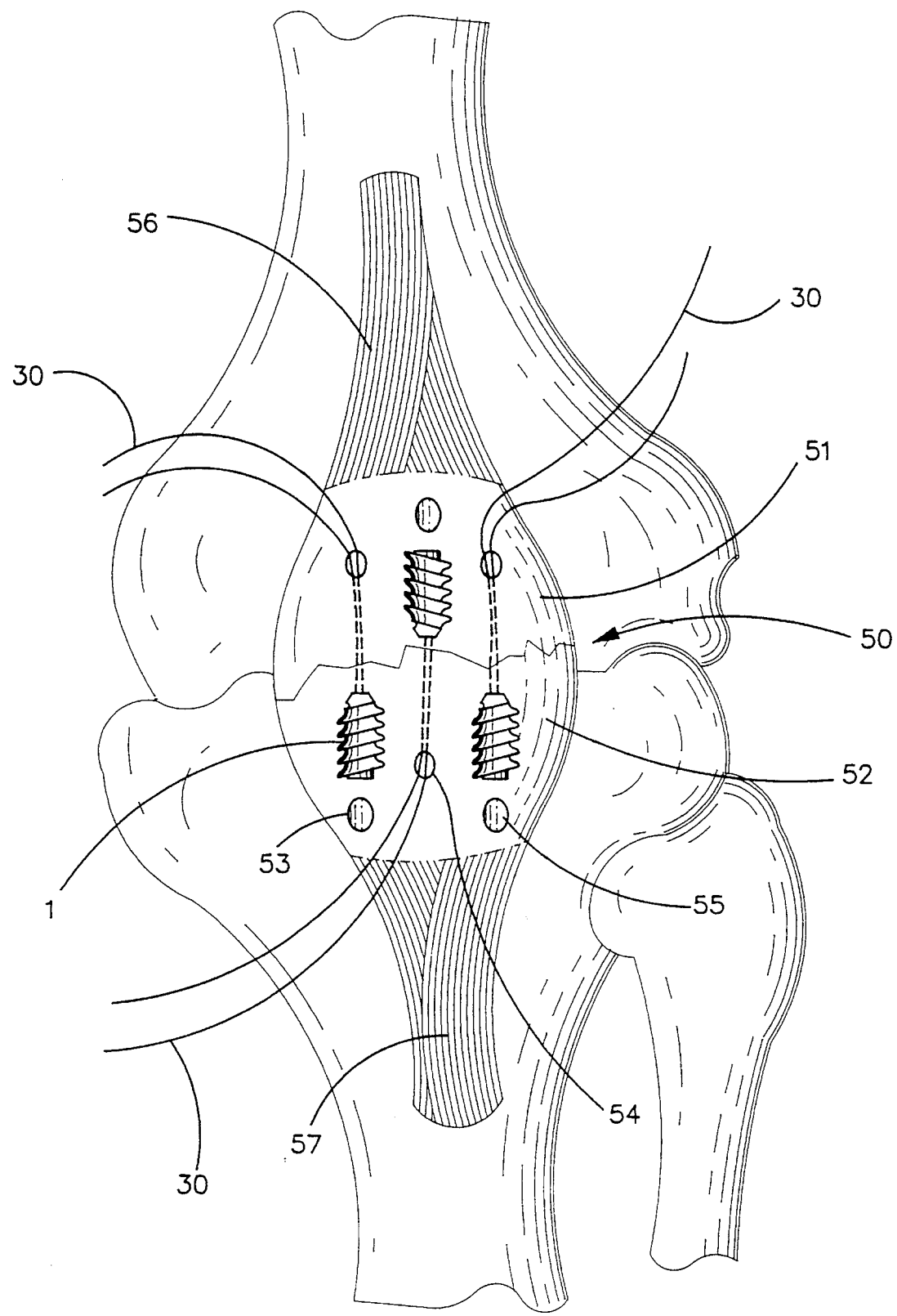
FIG. 4A is a front view of the embodiment of FIG. 1 used in a patella fracture with sutures extending only from the distal end of the anchor.
Figure 4B:
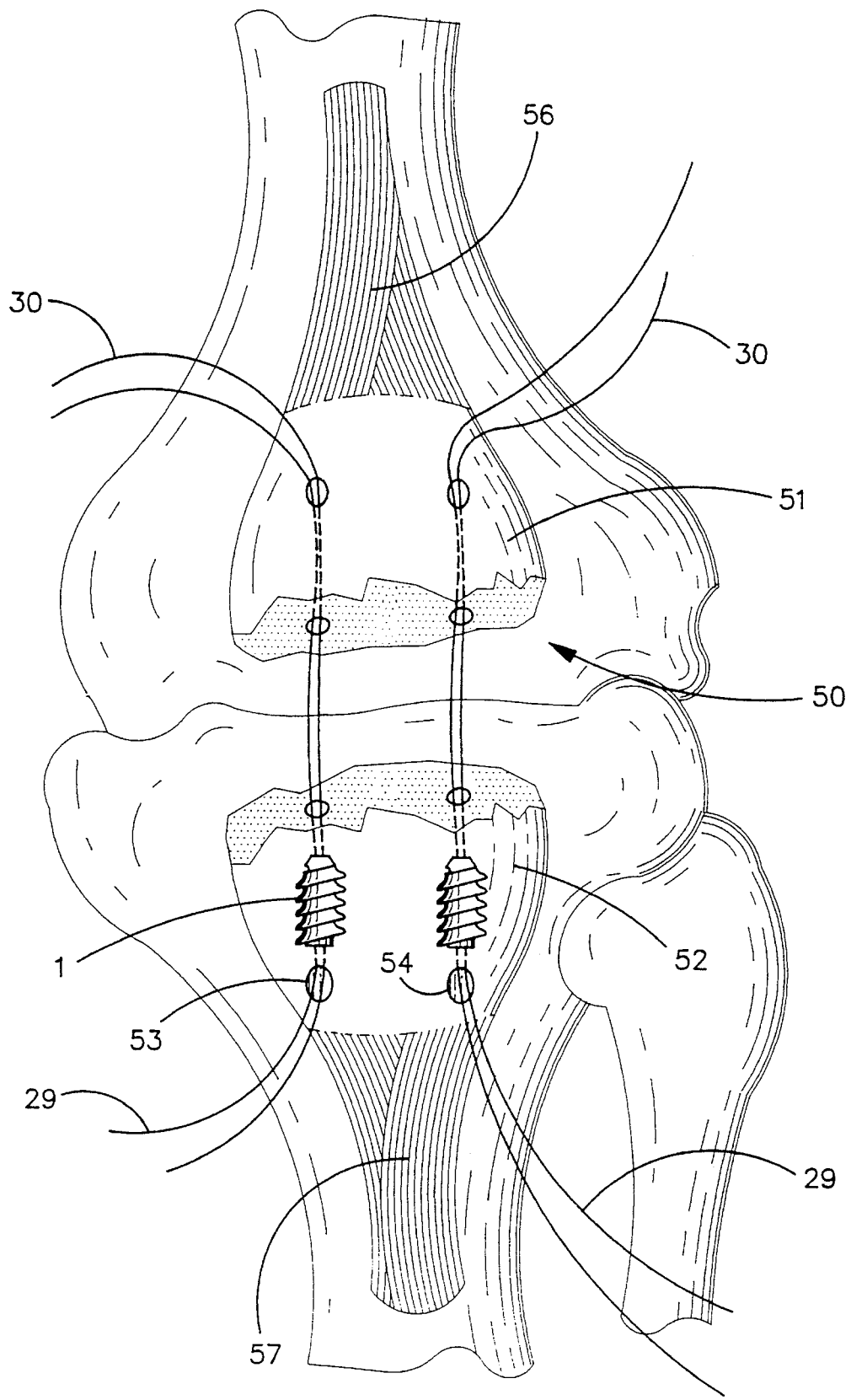
FIG. 4B is a front view of the embodiment of FIG. 1 used in a patella fracture with sutures extending from both ends of the anchor.
Figure 5:
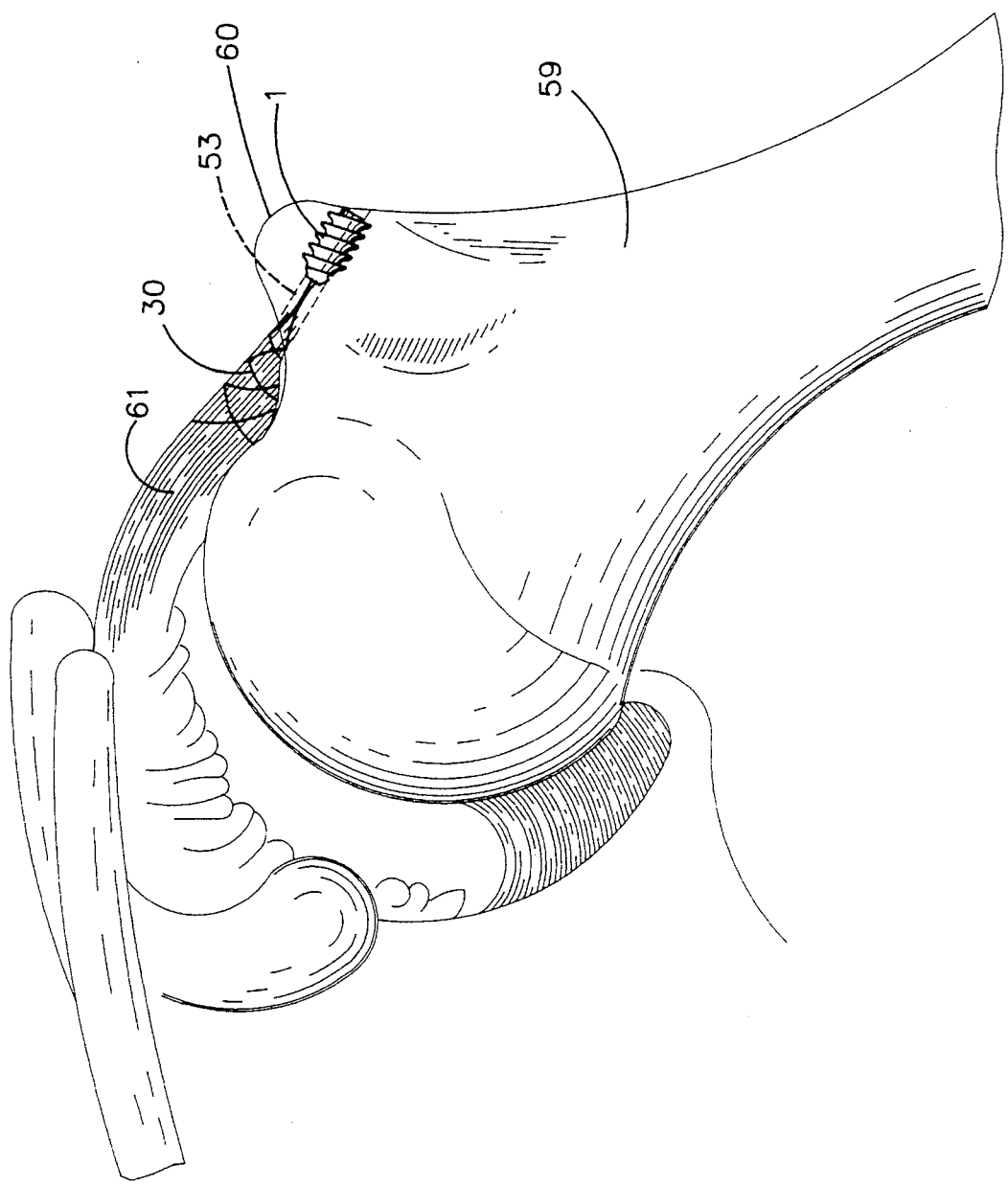
FIG. 5 is a side view of the embodiment of FIG. 1 used in a rotator cuff repair.

FIGS. 4A, 4B, and 5 illustrate three surgical applications of the preferred embodiment which will clarify the advantages of the present invention. FIG. 4A depicts a plurality of bidirectional anchors used to repair a nondisplaced patella fracture. Without displacing the fractured portions 51,52 of the patella 50, pilot holes 53–55 are formed completely across the patella 50. Suture threads, such as second suture thread 30, are drawn through each anchor 1 and its respective pilot hole, and the suture is tied off to create second suture thread knot 28 within the proximal portion 26 of each anchor 1. Thereafter, the anchors 1 are inserted with the appropriate driving tool into the pilot holes 53–55. Finally, the suture threads 30 extending from the distal end 17 of each anchor 1 may be tied to any adjacent suture threads or to nearby ligaments 56 or 57. As will be appreciated by orthopedic surgeons and others involved in these types of surgical procedures, the present invention does not require the patella to be displaced prior to insertion of the anchors. The result is less trauma to the affected tissue and decreased time spent in surgery.

FIG. 4B also depicts a patella fracture, but one in which the patella fragments 51,52 are clearly displaced. In this example, the bidirectional feature of the invention is shown. As with the previous example, pilot holes 53,54 are formed into the bone, and the bidirectional anchors 1 are inserted into the distal patella fragment 52. However, rather than using sutures in only one direction, the patella 50 is repaired by combining first and second suture threads 29,30 in both directions. In this manner, suture threads 30 may be tied to each other or to ligament 56. Likewise, suture threads 29 may be tied to each other or to ligament 57 for added strength and stability of the repair.

Finally, FIG. 5 illustrates the invention applied to a rotator cuff repair. The inclusion of the proximal portion 26 allows the anchor 1 to be inserted into the more lateral aspect 60 of the humeral shaft 59 in an opposite direction from that of the Ogden anchor. The bidirectional anchor 1 is inserted directly into the harder cortical bone so that second suture threads 30 extend from the pilot hole 53. Importantly, the anchor 1 is positioned so that it contacts as much cortical bone as possible. Once the anchor 1 is properly situated, the cuff 61 is attached using second suture thread 30. A distinct advantage of conducting the repair in this manner is that more cortical bone is in contact with the screw threads of the anchor 1, resulting in stronger retention of the cuff 61. Another advantage is that the insertion of the anchor 1 into the lateral aspect of the humerus, as opposed to insertion in the opposite direction like the Ogden screw, avoids disturbance of the cancellous bone from which the sutures extend. This is so because the anchor threads do not deform the bone ahead of the distal end of the anchor, as shown in FIG. 5, resulting in greater pull-out strength. In addition, the cuff 61 may be pulled further into the pilot hole 53 because there is no obstruction (such as a prior art anchor) to prevent the necessary contact between the cuff 61 and the bone mass. Finally, if additional sutures, such as first suture thread 29 were included in the manner described by Ogden, those sutures 29 from adjacent anchors 1 could be tied to one another for additional pull-out strength. As will be understood to those of ordinary skill, the foregoing advantages are especially important in severely osteoporotic patients.

An alternate embodiment 2 of the present invention is shown in FIG. 2 which adds bidirectional suture anchoring features to a commonly available bone fixation screw. The prior art bone fixation screw, such as the Acutrak device mentioned previously herein, is characterized by variable pitch, self-tapping, exterior screw threads 71 and a tapered or conical body 72. The length of the bone fixation screw 2 is relatively longer than the anchor 1, because it is intended to cross a bone fracture. The pitch of the threads 71, which increases from the distal portion 75 to the proximal portion 76, causes the bone fragments to close together during insertion of the screw 2, while the tapered body 72, which becomes increasingly wider from the distal portion 75 to the proximal portion 76, allows the threads 71 to purchase new bone with each revolution. The bone screw 2 includes a drive socket 73 similar to that of the preferred embodiment, and is also cannulated by passageway 74 so that its insertion alignment can be controlled by a guide pin (not shown).

Figure 4C:
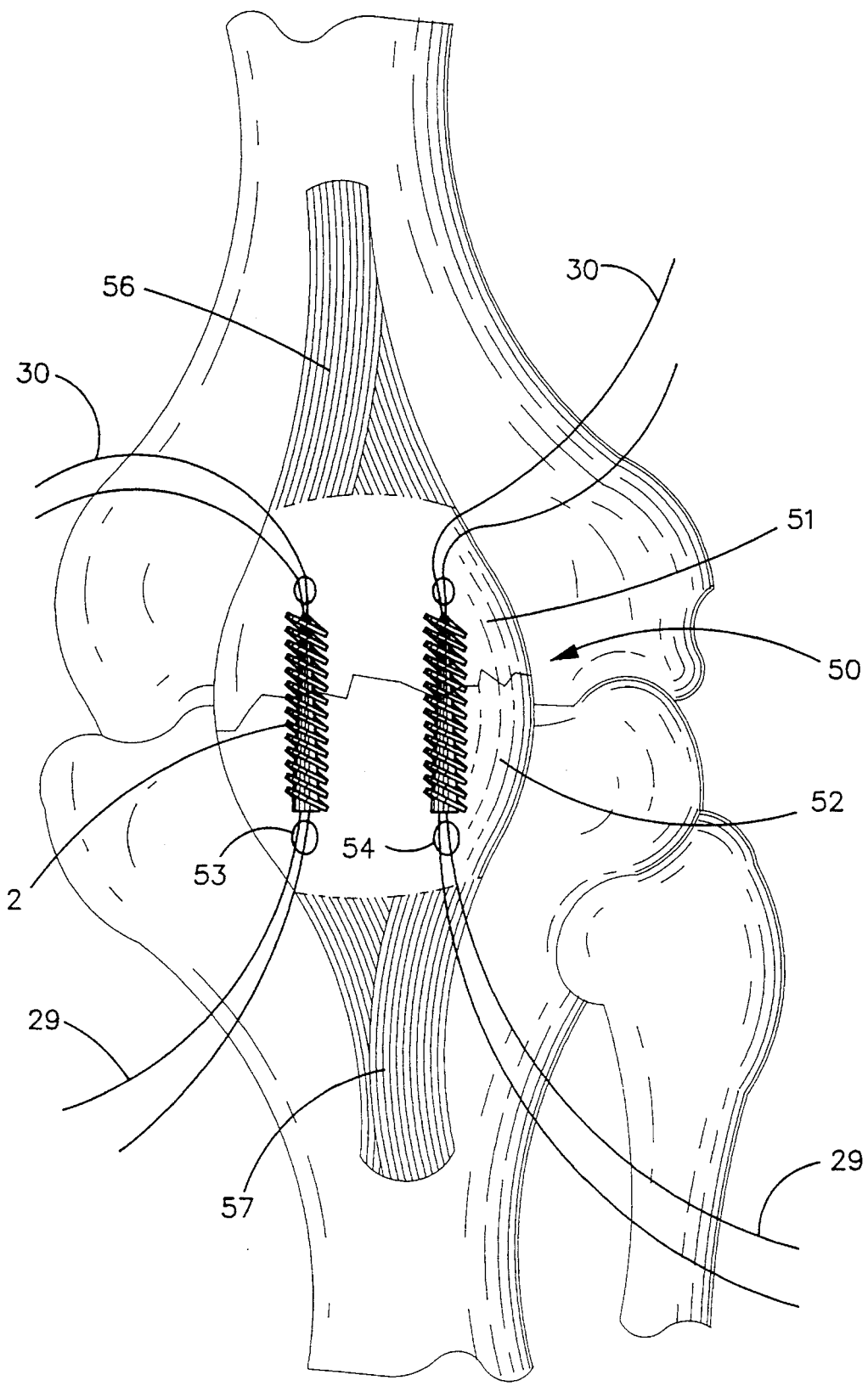
FIG. 4C is a front view of the embodiment of FIG. 2 used in a patella fracture with sutures extending from both ends of the anchor.

As discussed above, the prior art bone fixation screw has no suture anchoring capability. Consequently, the alternate embodiment includes a distal portion 75 and a proximal portion 76 identical in structure and function to the distal and proximal portions 25,26 seen in the preferred embodiment. Thus, all of the benefits of bidirectional suture anchoring can be achieved in addition to the desired fixation effects of the screw 2. For example, as shown in FIG. 4C, the alternate embodiment of the present invention is used to repair a patella fracture. The method of using the screw 2 is precisely the same as for the prior art bone fixation screw, but in addition to the steps explained above in relation to the suture anchoring techniques.

Significantly, the aforedescribed figures illustrate that the distal portions 25,75 in the preferred and alternate embodiments, respectively, may not be needed for certain surgical procedures. Thus, the preferred and alternate embodiments may also be manufactured without such features if desired. In such cases, suture threads would be anchored only in the proximal portions 26,76 of the applicable anchor or screw, and extending only from the distal end. While such configurations would not provide the bidirectional advantages explained previously herein, they would nonetheless provide all the other advantages inherent in anchoring the suture threads at the proximal portions 26,76 of the appropriate device.

Both the preferred and alternate embodiments described above may be constructed of any suitable biocompatible metal, such as stainless steel or titanium. In addition, the invention may also be constructed of a non-absorbable polymer such as Delrin polyacetal available from DuPont, or of a bioabsorbable material such as polylactic acid (lactide), polyglycolic acid (glycolide) disclosed in U.S. Pat. No. 3,739,773 (Schmitt, et al.), or copolymers disclosed in U.S. Pat. Nos. 4,300,565 (Rosensaft, et al.) and 4,429,080 (Casey, et al.), all of which are incorporated herein by reference. A combination of absorbable and nonabsorbable materials to form a partially absorbable anchor or bone screw can also be utilized.

The exterior surfaces of both embodiments may also be coated with an absorbable coating exhibiting a low coefficient of friction, such as polycaprolate. An acceptable polycaprolate copolymer is a random copolymer of 85 weight percent epsilon-caprolactone and 15 weight percent glycolide. Other suitable coatings are disclosed in U.S. Pat. No. 4,788,969 (Jarrett, et al.), which is incorporated herein by reference. In addition to reducing insertion torque, the absorbable coating can contain a pharmaceutical, a bone growth factor, or other compound. Additionally, the coating can have a selected absorption property to disappear within a desired period to enhance bone ingrowth and attachment to the anchor or bone screw, as applicable.

As a coating over an absorbable body of the anchor or bone screw, the absorbable coating can serve as a barrier to body fluids to affect the rate of absorption of the material. An absorbable coating according to the invention has a different composition than the body of the anchor or bone screw to provide one or more different selected properties such as a different coefficient of friction or rate of absorption.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A cannulated bone screw for anchoring a suture thread to bone, comprising:
    (a) a biocompatible body having a proximal end and a distal end, said body including exterior screw threads for inserting and retaining said body into the bone;
    (b) a passageway extending through said body, said passageway including a central portion, a proximal portion, and a distal portion, the central portion being sized to receive a suture thread therethrough, the proximal portion being sized to receive a suture thread knot, the distal portion being sized to receive a suture thread knot, the central portion being sized smaller than the proximal portion and the distal portion, the central portion being sufficiently small as to prevent a suture thread knot from being drawn therethrough; and
    (c) a drive socket, formed into said proximal end of said body, said drive socket being sized to prevent a drive tool from contacting a suture thread knot within said proximal portion of said passageway.

2. The bone screw of claim 1, wherein said exterior screw threads are self-tapping.

3. The bone screw of claim 1, wherein said body is cylindrical and includes a central axis, and wherein said passageway extends axially therethrough.

4. The bone screw of claim 3, wherein said body is constructed of a biocompatible material selected from the group consisting of a metal, a non-absorbable polymer, and a bioabsorbable material.

5. The bone screw of claim 4, wherein said biocompatible material is coated with a bioabsorbable coating having a low coefficient of friction.

6. The bone screw of claim 5, wherein said coating includes one or more compounds selected from the group consisting of pharmaceuticals and bone growth factors.

7. A method of attaching suture thread to bone, comprising the steps of:
    (a) providing a bone screw comprising a biocompatible body having a proximal end and a distal end, said body including exterior screw threads for inserting and retaining said body into the bone; a passageway extending through said body, said passageway including a central portion and a proximal portion, the central portion being sized to receive a suture thread therethrough, the proximal portion being sized to receive a suture thread knot, the central portion being sized smaller than the proximal portion, the central portion being sufficiently small as to prevent a suture thread knot from being drawn therethrough; and a drive socket, formed into said proximal end of said body, said drive socket being sized to prevent a drive tool from contacting a suture thread knot within said proximal portion of said passageway;
    (b) passing a first suture thread through the passageway of the body of said bone screw to extend from the proximal end;
    (c) tying a first knot in the first suture thread extending from the proximal end of the passageway;
    (d) withdrawing the first suture thread from the distal end of said bone screw until said first knot is received by the proximal portion and said first knot abuts the central portion;
    (e) passing said first suture thread through a pilot hole in said bone; and
    (f) inserting said bone screw into the bone.

8. The method of claim 7, wherein said passageway further includes a distal portion sized to receive a suture thread knot, the central portion being sized smaller than the distal portion; and wherein said method further includes the steps of, prior to passing said first suture thread through said pilot hole:
    (a) passing a second suture thread through the passageway of the body of said bone screw to extend from the distal end;
    (b) tying a second knot in the second suture thread extending from the distal end of the passageway; and
    (c) withdrawing the second suture thread from the proximal end of said bone screw until said second knot is received by the distal portion and said second knot abuts the central portion.

* * * * *